(12) United States Patent
Brudermüller et al.

(10) Patent No.: US 6,201,160 B1
(45) Date of Patent: Mar. 13, 2001

(54) PREPARATION OF ALCOHOLS

(75) Inventors: Martin Brudermüller, Mannheim; Matthias Irgang, Heidelberg; Martin Schmidt-Radde, Beindersheim; Franz Merger, Frankenthal; Tom Witzel, Ludwigshafen; Detlef Kratz, Heidelberg; Eckehard Danz, Ludwigshafen; Arnold Wittwer, Neustadt; Michael Hesse, Schifferstadt; Manfred Sauerwald, Meckenheim; Cristina Freire Erdbrügger, Bobenheim-Roxheim, all of (DE)

(73) Assignee: BASF Aktiengesellschaft, Ludwigschafen (DE)

( * ) Notice: Subject to any disclaimer, the term of this patent is extended or adjusted under 35 U.S.C. 154(b) by 0 days.

(21) Appl. No.: 08/737,736
(22) PCT Filed: May 19, 1995
(86) PCT No.: PCT/EP95/01920
  § 371 Date: Nov. 19, 1996
  § 102(e) Date: Nov. 19, 1996
(87) PCT Pub. No.: WO95/32171
  PCT Pub. Date: Nov. 30, 1995

(30) Foreign Application Priority Data

May 19, 1994 (DE) ................................. 44 17 622

(51) Int. Cl.$^7$ ....................................... C07C 27/04
(52) U.S. Cl. ........................ 568/862; 502/305; 502/318; 502/345; 568/727; 568/799; 568/891
(58) Field of Search ..................................... 568/727, 799, 568/891, 862; 502/305, 318, 35

(56) References Cited

U.S. PATENT DOCUMENTS 3,803,055 * 4/1974 Reich .

FOREIGN PATENT DOCUMENTS

2538253 * 10/1976 (DE) .
3933661 * 4/1991 (DE) .

* cited by examiner

Primary Examiner—Michael L. Shippen
(74) Attorney, Agent, or Firm—Keil & Weinkauf

(57) ABSTRACT

Alcohols are prepared by the catalytic hydrogenation of the corresponding carbonyl compounds at elevated temperatures and at superatmospheric pressure in the liquid phase by a process in which the catalyst used contains copper on an $SiO_2$-containing carrier in the presence or absence of one or more of the elements magnesium, barium, zinc and chromium.

20 Claims, No Drawings

PREPARATION OF ALCOHOLS

The present invention relates to the preparation of alcohols by catalytic hydrogenation of the corresponding carbonyl compounds. The present invention relates in particular to the use of novel catalysts for this hydrogenation.

The present invention provides in particular a novel process for the preparation of diols from the corresponding aldehydes. A particular application is the preparation of propanediols.

Propanediols and their industrially most important member, neopentylglycol, are intermediates having a broad range of applications in the plastics industry, especially for manmade fibers, polyurethanes and plasticizers.

Neopentylglycol is prepared by condensation of isobutyraldehyde with formaldehyde and subsequent catalytic hydrogenation of the resulting hydroxypivalaldehyde. This hydrogenation has been described in many publications.

Known catalytically active elements for the hydrogenation of alcohols are Ni, Ru, Pt, Re and Cu.

Ni-containing catalysts are mentioned in the patents DE 19 57 592 (1971), DE 20 54 601 (1972) and SE 454 171 (1988). DE 16 43 856 describes the hydrogenation of saturated and unsaturated aldehydes to give alcohols or combined Cu/Ni supported catalysts in the gas phase. However, a disadvantage of Ni-containing catalysts is their considerable tendency to form byproducts, as described in EP 0 044 412.

Noble metal-containing catalysts are described in EP 0 343 475 (Pt-Ru-W), EP 0 373 938 (Re) and SU 361998 (Ru-Ni-Cr). Owing to their high price, these catalysts are however not very suitable for large scale industrial use.

Owing to their wide range of advantages over catalysts containing nickel and noble metal, copper-catalysts form containing the most important group of hydrogenation catalysts for the preparation of alcohol in practice. In particular, Cu—Cr catalysts have a wide range of applications. However, they have the disadvantage that high space-time yields can be achieved only by means of relatively high pressures and temperatures during the hydrogenation. Catalysts of this type are described in U.S. Pat. No. 4,855,515, DE 18 04 984 and JP 49 011 684.

However, these catalysts, too, have been found to have a high tendency to form byproducts, which is described in DE 40 37 729 and U.S. Pat. No. 4,666,879.

However, the properties of the catalyst depend not only on the choice of the catalytically active component but also decisively on the choice of the carrier.

Thus, copper catalysts having carriers containing $Al_2O_3$ or ZnO are described in EP 0 044 444 ($CuO/Al_2O_3$), EP 0 044 412 (CuO/ZnO) and EP 0 484 800 ($CuO/ZnO/ZrO_2$). The $CuO/Al_2O_3$ catalysts and CuO/ZnO catalysts initially have high activity and selectivity but also exhibit pronounced aging. A further problem in the case of $Al_2O_3$-containing catalysts is the rehydration which occurs at relatively high temperatures and is caused by the use of the starting material in aqueous solution and may lead to disintegration of the catalysts.

The use of $ZrO_2$-containing carrier gives stable catalysts which, however, owing to the high content of $ZrO_2$, have virtually twice as high a bulk density as the $Al_2O_3$-containing catalysts.

However, the properties of the copper catalysts used depend not only on the choice of the active component and of the total composition but also decisively on the conditions of the preparation process. A number of processes for the preparation of copper catalysts for the hydrogenation of carbonyl compounds are known.

Thus, DE 41 42 897 describes the preparation of copper catalysts having small copper particles and a correspondingly large effective surface area of the catalyst material by precipitation of the copper-containing component. However, this process generally leads to unsatisfactory results in spite of considerable expense.

According to EP 0 006 313, small copper crystallites can also be obtained by precipitation of a copper compound at elevated temperatures onto an inert carrier.

The preparation of catalysts having high copper contents by precipitation is furthermore described in FR 1520584.

U.S. Pat. No. 3,701,739 describes a process for the preparation of Cu/Zn catalysts by agglomeration of copper-containing particles in a fluidized bed and subsequent decomposition of the agglomerated components. However, the disadvantage of catalysts prepared in this manner is their relatively low mechanical hardness.

Important criteria for the suitability of the catalysts which can be used in these processes are not only their activity and selectivity for the catalyzed reaction but also their mechanical properties, such as hardness and abrasion resistance. The mechanical properties of the catalysts used are therefore of particular importance for the cost-effectiveness of the process, because insufficient mechanical stability of the catalyst may lead in a relatively short time to blockage of the plant owing to pronounced catalyst abrasion, resulting in long downtimes.

It is an object of the present invention to provide a process which permits the preparation of alcohols from the corresponding carbonyl compounds in an economical manner and with good yield and selectivity. For this purpose, it was intended to provide catalysts which permit this reaction with high activity and selectivity and which possess good mechanical properties, in particular great hardness and abrasion resistance, and, advantageously, a low bulk density. These catalysts should also be capable of being prepared in an economical manner.

We have found that this object is achieved by the process, described in the claims, for the preparation of alcohols by catalytic hydrogenation of the corresponding carbonyl compounds at elevated temperatures and at superatmospheric pressure in the liquid phase. According to the invention, the catalyst used is one which contains copper on an $SiO_2$-containing carrier in the presence or absence of one or more of the elements magnesium, barium, zinc and chromium.

The catalyst used in the novel process for the preparation of alcohols is distinguished by the fact that the active component copper is applied to an $SiO_2$-containing carrier.

The carrier used for a catalyst is referred to as $SiO_2$-containing if it contains $SiO_2$ or a silicate, such as magnesium silicate. Since the anionic silicate groups are present in monomeric, oligomeric and polymeric form side by side in the catalyst, they are detected analytically and calculated as $SiO_2$.

The copper catalyst used for the novel process and having an $SiO_2$-containing carrier contains preferably from 5 to 75% by weight, calculated as CuO, of copper and from 95 to 25% by weight, calculated as $SiO_2$, of Si, based in each case on the total weight of the calcined catalyst.

Other catalysts which may be advantageously used in the novel process are those which, in addition to copper and silicon, contain one or more of the elements magnesium, barium, zinc and chromium. Magnesium is present in an amount of from 0 to 20% by weight, calculated as MgO, barium in an amount of from 0 to 5% by weight, calculated as BaO, zinc in an amount of from 0 to 5% by weight, calculated as ZnO, and chromium in an amount from 0 to 5% by weight, calculated as $Cr_2O_3$, based in each case on the total weight of the calcined catalyst, with the proviso that the sum of the catalyst components copper, silicon and, if present, magnesium, barium, zinc and chromium is 100% by weight.

The copper catalysts described, which have an $SiO_2$-containing carrier, can be prepared by the known and abovementioned processes.

In particular, the following preparation processes are suitable: Application of an aqueous copper salt solution in one or more impregnation stages to a prepared carrier consisting of $SiO_2$, magnesium silicate or another sparingly soluble silicate. A preferred carrier is $SiO_2$. The impregnated carrier is then dried and calcined.

The impregnation can be carried out by the incipient wetness method, in which the carrier is moistened according to its water absorptivity with the impregnating solution up to saturation. However, impregnation may also be effected in supernatant solution. In multistage impregnation processes, it is advantageous to carry out drying and, if required, calcination between the individual impregnation steps. Multistage impregnation is particularly advantageous when a relatively large amount of copper is to be deposited on the carrier.

It is also possible to use a pulverulent carrier, for example powdered $SiO_2$ or powdered alkaline earth metal silicate. This is generally kneaded after impregnation, molded and calcined. Precipitation of a sparingly soluble copper compound, such as copper carbonate or copper hydroxide, from an aqueous solution onto pulverulent $SiO_2$ or alkaline earth metal silicate, which is initially taken as a suspension.

The precipitated catalyst can also be prepared in two stages by first precipitating the carrier from waterglass by adding acid and, in a second stage, precipitating a sparingly soluble copper salt. The precipitation of the sparingly soluble copper compounds and silicon compounds can also be carried out simultaneously by passing a copper salt solution into a waterglass solution.

Precipitates are filtered in a conventional manner, preferably washed alkali-free, dried and, if required, calcined. Molding is then effected by kneading and extrusion or by pelletizing.

Copper catalysts which have been prepared by impregnation of silica with a supernatant aqueous solution of a thermally readily decomposable copper compound and by subsequent drying and calcination, are particularly advantageously used in the novel process. The calcination is effected in general at from 200 to 400° C., preferably from 250 to 350° C.

Such copper catalysts contain in general from 5 to 50, preferably from 5 to 30, % by weight, calculated as CuO, of copper, and from 50 to 95, preferably from 70 to 95, % by weight, calculated as $SiO_2$, of silicon, based in each case on the total weight of the calcined catalyst.

Impregnation with a supernatant solution leads to a relatively uniform impregnation of the carrier and hence to a finer and more uniform distribution of the copper in the carrier. The formation of nonuniform concentration profiles over the cross-section of the carrier, as may occur in impregnation by the incipient wetness method, are avoided in this process, with the result that the preparation of the catalysts to be used according to the invention is more reproducible and consequently more economical.

The use of copper compounds which are decomposable at from 200 to 400° C., preferably from 250 to 350° C., accordingly permits lower calcination temperatures. This promotes the formation of relatively small copper particles and their uniform distribution over the carrier material.

The catalysts prepared by the novel process therefore have a relatively larger effective copper surface area. Both impregnation in a supernatant solution of a conventionally used copper salt, such as copper nitrate, and the use of copper compounds which are decomposable at a relatively low temperature have the stated advantages. However, the best effect is achieved if impregnation is effected in supernatant solution and a readily decomposable copper compound is used.

The dispersion is a measure of the effective copper surface area for a certain amount of copper used. It is defined as the ratio of the number of copper atoms on the surface of the copper crystallites to the total number of copper atoms in the copper crystallites of the carrier.

The dispersion of the copper in a catalyst can be determined directly from the size of the crystallites or indirectly from the amount of oxygen required to oxidize the copper surface and the amount of copper used in the impregnation.

The size of the copper crystallites can be determined directly by transmission electron microscopy (TEM) using an ultrathin disk of the ready-made copper catalyst, produced in an ultramicrotome after fixation with polymethyl methacrylate. Particle sizes up to 1 nm can be determined in this manner. From the size of the copper crystallites, it is then possible to calculate the dispersion of the copper directly.

In addition, the phase of the copper-containing particles can be determined by Energy Dispersive X-ray Spectroscopy (EDX-S) or Selected Area Diffraction (SAD).

In the indirect method for determining the dispersion, the dispersion of the copper in the catalyst carrier is calculated from the amount of oxygen consumed in the oxidation of the copper surface and the amount of copper contained in the carrier.

An accurately weighed sample of the ready-made catalyst is flushed with helium for one hour, heated to 200° C. under reduced pressure and then reduced with hydrogen for 16 hours. After complete reduction, evacuation is effected again. The sample is then left to cool to 35° C., and the oxygen chemisorption is determined by a volumetric sorption method, the oxygen chemisorption being measured at at least four different points in the pressure range from 50 to 250 mmHg (from 66.65 to 33.25 mbar) (apparatus: eg. Chemisorb 2810 from Micromeretics). Starting with the assumption that two copper atoms react with each oxygen atom, it is possible to calculate the copper surface area. The amount of copper in the catalyst sample can be determined by simple analysis. The dispersion of the copper in the catalyst is obtained in percent from the ratio of the number of copper atoms, determined in this manner, at the copper surface to the total number of copper atoms in the measured catalyst sample, multiplied by 100.

In addition to high dispersion, however, the catalysts prepared by the novel process also have improved mechanical stability. In particular, greater hardness and reduced abrasion of the catalyst are typical of the increased mechanical stability.

These parameters can be determined as follows. To determine the cutting hardness, samples are cut by means of a blade. The force which has to be applied to the blade in order to cut through the sample is referred to as the cutting hardness of the material.

The fracture hardness of spherical samples is determined by placing the sphere under a ram having a defined area and then moving the ram against the sphere until the latter breaks. The pressure exerted on the sample by the ram and required to achieve fracture is referred to as the fracture hardness.

The abrasion is determined in a vibratory mill. Catalyst material having a certain particle size range is agitated together with porcelain beads in a container at high speed for a certain period. The catalyst is then separated off by sieving. The weight loss in percent is then referred to as abrasion.

For the purposes of the novel process, a catalyst which has been obtained by impregnation of a porous silica carrier with a supernatant aqueous solution of a thermally readily decomposable copper compound using an impregnation time of from 2 to 60, preferably from 5 to 30, minutes and subsequent drying and calcination is preferably used.

In particular, catalysts which have been obtained by impregnation of a porous silica carrier having a BET surface area of more than 100 $m^2/g$ with a supernatant aqueous solution of a thermally readily decomposable copper compound and subsequent drying and calcination are preferably used in the novel process.

Thermally readily decomposable copper compounds are understood as meaning copper compounds which decompose at calcination temperatures of from 200 to 400° C., preferably from 250 to 350° C., into oxidic copper compounds or elemental copper. Examples of such compounds are copper carbonate, copper oxalate and copper formate. Since some of these copper salts as such are sparingly soluble and the solutions of many of these salts tend to hydrolyze, these copper salts are preferably used in the impregnation solution in the form of their relatively stable, readily water-soluble complexes with ammonia, hydrazine or amines, preferably in the form of their ammine complexes. Ammoniacal copper carbonate solution is particularly preferably used for this purpose. The use of these copper compounds which readily undergo thermal decomposition permits calcination at the stated low temperatures, whereas copper salts conventionally used for impregnation, such as copper nitrate or copper sulfate, generally require calcination temperatures of about 500° C. Both the use of copper compounds which readily undergo thermal decomposition and the use of low calcination temperatures permit the production of small copper crystallites and hence a larger catalytically active copper surface area in the ready-made catalyst.

For the purpose of the present invention, it is therefore possible in principle to use all copper compounds which decompose at relatively low temperatures, ie. at less than 400° C., at atmospheric pressure.

The novel process can be carried out under conditions such as those usually used in hydrogenation processes. However, the conditions stated below are preferred.

The hydrogenation reactor can be operated in the liquid phase or trickle-bed procedure. As a rule, it is advantageous to recycle some of the hydrogenated product to the hydrogenation process (circulation method).

Before being used in the novel process, the catalyst is preferably reduced beforehand with reducing gases, for example hydrogen, preferably with hydrogen inert gas mixtures, in particular hydrogen/nitrogen mixtures, from 100 to 300° C., preferably from 150 to 250° C.

The catalyst space velocity in the hydrogenation is preferably from 0.1 to 1.0 l of carbonyl compound per l of catalyst per h. Thus, from 0.1 to 1 liter of carbonyl compound flows through the catalyst volume of 1 liter per hour.

The carbonyl compounds are preferably hydrogenated at from 60 to 200° C., preferably from 80 to 160° C., and at from 1 to 150, preferably from 20 to 100, bar, a pH of from 4 to 13, preferably from 6 to 12, particularly preferably from 7 to 12, being maintained in the liquid phase.

The novel process can in principle be used for the hydrogenation of any desired carbonyl compounds to alcohols. However, the novel process is particularly advantageous for the hydrogenation of some carbonyl compounds stated below.

For example, $C_2$–$C_{20}$-hydroxyaldehydes and $C_2$–$C_{20}$-hydroxyketones can advantageously be hydrogenated to the corresponding alcohols by the novel process. These hydroxycarbonyl compounds may contain one or more hydroxyl groups. Thus, the novel process is very suitable for the hydrogenation of polyhydroxycarbonyl compounds, in particular of carbohydrates, such as glucose, fructose, mannose or xylose, the corresponding sugar alcohols, such as sorbitol, mannitol or xylitol, being formed from these sugars and being used as sugar substitutes.

The novel process is particularly advantageously used for the hydrogenation of $C_2$–$C_{20}$-monohydroxyaldehydes to the corresponding alcohols. In this process, preferably hydroxypropionaldehydes of the general formula I

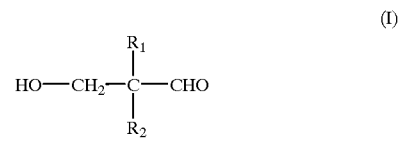

(I)

are used as carbonyl compounds and are converted into 1,3-propanediols of the general formula II

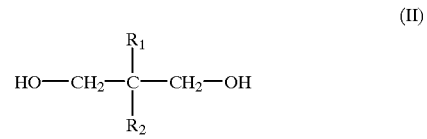

(II)

where $R^1$ and $R^2$ are identical or different and are each hydrogen, $C_1$–$C_{24}$-alkyl, $C_6$–$C_{20}$-aryl and/or $C_7$–$C_{12}$-aralkyl or the two radicals $R^1$ and $R^2$, together with the neighboring carbon atoms, form a 5-membered to 10-membered alicyclic ring.

Hydroxypivalaldehyde (HPA) of the formula Ia

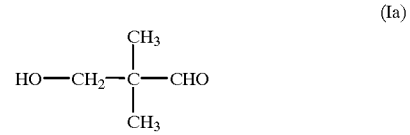

(Ia)

is particularly advantageously used as the carbonyl compound of the novel process and is converted into neopentylglycol (NPG) of the formula IIa

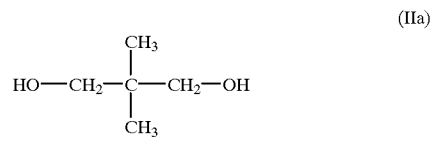

(IIa)

The hydrogenation yield is extremely high and is even close to 100% when the preferred catalysts are used, also at very high space velocities. Formation of byproducts, such as esters and acetals, which adversely affects the cost-effectiveness of the process could not be detected. There is also no evidence of cleavage of hydroxypivalaldehyde back into isobutyraldehyde and formaldehyde.

In a preferred embodiment of the process for the preparation of NPG, the following steps are carried out in succession:

Isobutyraldehyde and formaldehyde are reacted in an aqueous medium in the presence of a trialkylamine to give HPA, unconverted isobutyraldehyde and, if technically unavoidable, trialkylamine from the aqueous solution are separated off from the reaction solution, preferably by distillation, fresh or isolated trialkylamine is preferably added to the HPA solution freed from unconverted isobutyraldehyde, until the solution has reached a pH of from 4 to 13, preferably from 6 to 12, particularly preferably from 7 to 12, the resulting HPA solution, which, in addition to hydroxypivalaldehyde, contains trialkylamine and other impurities and byproducts from the reaction of isobutyraldehyde with formaldehyde, is hydrogenated with hydrogen in the presence of a copper catalyst to be used according to the invention, and neopentylglycol is recovered from the hydrogenated solution, preferably by distillation.

The isobutyraldehyde/trialkylamine mixture obtained in the distillation of the reaction solution from the condensation of isobutyraldehyde with formaldehyde can advantageously be used again for the condensation reaction. The condensation reaction of isobutyraldehyde with formaldehyde can preferably be carried out by the method as described in U.S. Pat. No. 3,808,280, which is hereby incorporated by reference.

Another preferred carbonyl compound is 2-hydroxymethyl-2-methylbutanal of the formula Ib

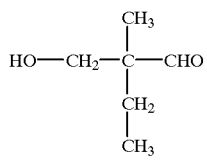

(Ib)

which is converted into 2-methyl-2-ethyl-1,3-propanediol of the formula IIb

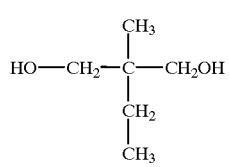

(IIb)

In comparison, the use of 1-formyl-1-hydroxymethylcyclopentane of the formula Ic

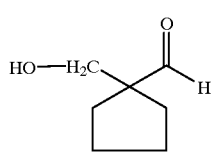

(Ic)

as the carbonyl compound is particularly preferred. This is converted into 1,1-bis(hydroxymethyl)cyclopentane of the formula IIc.

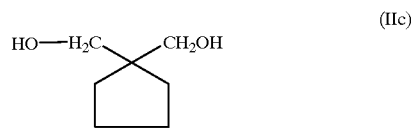

(IIc)

It should be emphasized that the above statements serve merely as examples for illustrating the virtually universal applicability of the novel process for the preparation of alcohols from hydroxycarbonyl compounds.

With the aid of the novel process, the corresponding alcohols can also advantageously be prepared from other carbonyl compounds, for example straight-chain or branched aliphatic aldehydes of 1 to 24 carbon atoms, straight-chain or branched aliphatic ketones of 1 to 24 carbon atoms or alicyclic $C_4$–$C_{12}$-ketones. The alcohols obtained thereby are used, for example, as solvents or as intermediates in the preparation of surfactants and dispersions. The hydrogenation of propionaldehyde to n-propanol, butyraldehyde to n-butanol, isobutyraldehyde to isobutanol, valeraldehyde to n-pentanol, 2-ethylhexanal to 2-ethylhexanol, acetone to isopropanol, methyl ethyl ketone to 2-butanol, cyclopentanone to cyclopentanol and cyclohexanone to cyclohexanol may be mentioned merely by way of example. Mixtures of these carbonyl compounds may also be used as starting material in the novel process. A particular advantage of the novel process is that the copper catalysts to be used according to the invention are relatively insensitive to typical impurities in the starting materials for the hydrogenation, for example acetals, carboxylic acids, etc. The starting materials can thus be used in the novel process without expensive preliminary purification. For example, butanal/isobutanal mixtures, as obtained in the hydroformylation of propene, can be fed directly to the hydrogenation.

The novel process is also very suitable for the preparation of the corresponding saturated alcohols from straight-chain or branched aliphatic $C_3$–$C_{12}$-α,β-unsaturated carbonyl compounds. Examples here are the hydrogenation of acrolein to n-propanol, of crotonaldehyde to n-butanol, of 2-ethylhex-2-en-1-al to 2-ethylhexanol and of 2-propylhept-2-en-1-al to 2-propylheptanol. 2-Ethylhexanol and 2-propylheptanol are industrially important plasticizer alcohols. In the hydrogenation of these α,β-unsaturated carbonyl compounds, too, the starting materials may be fed to the novel process in technical quality without prior fine purification, this having no adverse effect on the results of the process.

EXAMPLE 1

Table I shows a comparison of the copper catalysts on an $SiO_2$-containing carrier, which catalysts are intended for the novel process, with conventional copper catalysts, using the hydrogenation of hydroxypival-aldehyde as an example.

The catalysts are prepared in the following manner:

Catalyst A 1000 g of a commercial $SiO_2$ catalyst carrier having a porosity of 1.0 ml/g and a BET surface area of about 200 $m^2$/g were impregnated with 1000 ml of an ammoniacal copper carbonate solution. After complete absorption of the solution, the carrier was dried and was calcined at 500° C.

A second impregnation was then carried out in the same manner, and drying and calcination were once again effected.

The prepared catalyst contained 25% by weight of CuO, based on the total weight of the catalyst. It had a bulk density of 625 g/l, a BET surface area of 150 m²/g and a porosity of 0.6 ml/g. Catalyst A had a cutting hardness of 18 N.

Catalyst B 2.8 kg of an ammoniacal copper carbonate solution which contained 14.3% by weight, based on the total weight of the solution, of Cu were slowly added to 1.5 kg of a pulverulent precipitated silica (BASF, D11-10 powder) in a kneader. Kneading was carried out for one hour, after which the material was molded in an extruder, then dried and calcined at 500° C.

The catalyst had a bulk density of 475 g/l and contained 24% by weight, based on the total weight of the catalyst, of CuO. Catalyst B had a cutting hardness of 28.4 N.

Catalyst C

A solution of soda waterglass which contained 1.9 kg of $SiO_2$ and a solution of magnesium nitrate containing the equivalent of 1.0 kg of MgO were simultaneously pumped into a stirred vessel at room temperature. The resulting pH was about 10. Thereafter, a mixed solution of copper nitrate/barium nitrate/zinc nitrate/chromium nitrate and a sodium carbonate solution were simultaneously added so that the resulting pH was 7.8.

The total precipitate was thoroughly washed on a filter press, the filter cake was dried and was calcined to a loss on ignition of 15% and the powder thus formed was pelletized.

The prepared catalyst contained 60% by weight of CuO, 13% by weight of MgO, 25% by weight of $SiO_2$, 1% by weight of BaO, 0.5% by weight of ZnO and 0.5% by weight of $Cr_2O_3$, based in each case on the total weight of the catalyst. It had a bulk density of 1050 g/l. The cutting hardness was 97 N and the abrasion 6%.

Catalyst D=Comparative Example

An ammonium bicarbonate solution was added to a copper nitrate solution and the suspension obtained was mixed with a ZnO suspension and gassed with carbon dioxide for 40 minutes at 70° C. A zirconyl nitrate solution and further ammonium bicarbonate were added to this mixture. Stirring was carried out for 30 minutes at 40° C., after which filtration and washing were effected.

The product contained, based on the total weight, 31% by weight of CuO, 67% by weight of $ZrO_2$ and 2% by weight of ZnO. It was dried, calcined at 350° C. and pelletized. The bulk density was 1900 g/l.

Catalyst E=Comparative Example

A mixed solution of copper nitrate and aluminum nitrate was prepared (weight ratio $CuO/Al_2O_3$=54/46) and this solution was pumped simultaneously with a sodium carbonate solution into a stirred container so that the pH remained constant at 5.5 during the precipitation. The pH was then increased to 7.0 and stirring was continued for 60 minutes while passing in air. During this procedure, the pH increased to 7.9. The temperature in the precipitation container was kept at 70° C. for the total time. The precipitated product was thoroughly washed on a filter press, dried and pelletized. The pellets were calcined at 620° C. for one hour. The catalyst had a bulk density of about 1000 g/l and a BET surface area of 80 m²/g and contained about 54% by weight, based on the total weight of the catalyst, of CuO.

In order to determine the mechanical properties of the catalysts, as stated in the Tables below, the methods described above were used. Specifically, the values were determined as follows:

To determine the cutting hardness, a commercial tester (manufacturer: NENE) having a 0.3 mm thick blade, a stationary plate and a freely movable horizontal ram was used.

The fracture hardness was measured using a commercial tester (manufacturer: Frank, type 1,557) having a ram diameter of 3 mm.

In the determination of the abrasion, the catalyst sample was passed through a 2 mm sieve. 100 g of the sample were then introduced, together with 30 g of porcelain balls having a diameter of from 10 to 11 mm and a weight of 1.7 to 2.0 g each, into a container which was rotated on a vibratory mill for 2 hours at 1400 revolutions. The material was then once again passed through a 2 mm sieve.

The hydrogenation of hydroxypivalaldehyde was carried out under the following conditions:

60 ml of the above catalysts in the form of extrudates, pellets or beads were installed in an electrically heatable tube reactor (volume=100 ml) and reduced with an $H_2/N_2$ gas mixture at from 150 to 240° C. After 5 hours, the proportion of hydrogen was increased to 100% and a hydrogen pressure of 30 bar was then established.

After the reduction, an aqueous solution containing 75% by weight, based on the total weight of the solution, of HPA was pumped linearly over the catalyst. The hydrogenation product was collected in a receiver and analyzed with the aid of gas chromatography (GC analysis).

The space velocity and the hydrogenation temperatures established are shown in Table I, together with the resulting conversions and selectivities and the amount of isobutanol formed as a byproduct for the stated catalyst.

The novel catalysts A, B and C have high activity and heat stability compared with the conventional catalysts D and E. The catalysts A and B furthermore have a substantially lower bulk density. Catalyst A moreover has a high selectivity and complete conversion up to high space velocities.

TABLE I

|  | Temp °C. | Space velocity $1_{HPA}/1_{Cat.} \cdot h$ | Conversion | Selectivity % | i-BuOH | CuO % by wt. | Other material % by wt. |
|---|---|---|---|---|---|---|---|
| Cat. A | 140 | 0.35 | 99.6 | 99.0 | 0.2 | 25 | 75 $SiO_2$ |
|  | 140 | 0.44 | 99.3 | 98.9 | 0.3 |  |  |
|  | 150 | 0.61 | 99.1 | 97.6 | 1.2 |  |  |
| Cat. B | 130 | 0.33 | 99.8 | 99.0 | 0.1 | 24 | 76 $SiO_2$ |
|  | 140 | 0.33 | 99.6 | 98.9 | 0.3 |  |  |
|  | 140 | 0.45 | 99.3 | 98.0 | 0.8 |  |  |
| Cat. C | 150 | 0.33 | 99.5 | 95.9 | 0.6 | 60 | 25 $SiO_2$ |
|  | 150 | 0.40 | 99.8 | 97.1 | 0.8 |  | 13 MgO |
|  | 150 | 0.50 | 99.8 | 95.8 | 0.9 |  | (Ba, Zn, Cr) |
| Cat. D | 140 | 0.33 | 87.8 | 83.1 | 4.1 | 31 | 67 $ZrO_2$ |

TABLE I-continued

|  | Temp °C. | Space velocity $l_{HPA}/l_{Cat.} \cdot h$ | Conversion | Selectivity % | i-BuOH | CuO % by wt. | Other material % by wt. |
|---|---|---|---|---|---|---|---|
| Comp. Expl. | 150 | 0.33 | 93.5 | 84.2 | 8.7 |  | 2 ZnO |
| Cat. E | 130 | 0.33 | 99.8 | 99.0 | 0.3 | 54 | 46 $Al_2O_3$ |
| Comp. Expl. | 130 140 | 0.40 | 98.7 Catalyst disintegration | 98.1 | 0.7 |  |  |

EXAMPLE 2

The properties of novel catalysts and catalysts not according to the invention are compared below in the novel process for the hydrogenation of a number of carbonyl compounds.

The catalysts are prepared in the following manner:

Catalyst F=Comparative Example

Catalyst F was prepared in the same way as catalyst E in Example 1.

Catalyst G $SiO_2$ beads having a diameter of from 3 to 5 mm were impregnated with a solution of copper carbonate in concentrated aqueous ammonia. This impregnation was carried out for 15 minutes in supernatant solution. The impregnated beads were then dried for 5 hours at 120° C. and then calcined for 2 hours at 300° C.

These impregnation and calcination steps were repeated once.

The copper content of the impregnation solution was adjusted so that the desired copper content of the catalyst was obtained after impregnation once or several times.

The prepared catalyst contained 25.6% by weight of CuO and 74.4% by weight of $SiO_2$, based in each case on the total weight of the catalyst.

Catalyst H

Catalyst H was prepared by impregnating 3 mm thick $SiO_2$ extrudates with an ammoniacal copper carbonate solution by the incipient wetness method. The impregnation solution was metered to the carrier in an amount which corresponded to its water absorptivity. Thereafter, drying was carried out and calcination was effected at 350° C.

The prepared catalyst contained 23.6% by weight of CuO and 76.4% by weight of $SiO_2$, based in each case on the total weight of the catalyst.

Catalyst I

The preparation was carried out similarly to the preparation of catalyst H. $SiO_2$ beads having a diameter of from 1.5 to 3 mm were used as the carrier.

The prepared catalyst contained 24.5% by weight of CuO and 75.5% by weight of $SiO_2$, based in each case on the total weight of the catalyst.

Catalyst J

The preparation was carried out similarly to the preparation of catalyst H, the $SiO_2$ beads described in the case of catalyst G being used as the carrier.

The prepared catalyst contained 23.7% by weight of CuO and 76.3% by weight of $SiO_2$, based in each case on the total weight of the catalyst.

Catalyst K $SiO_2$ extrudates having a diameter of 4 mm were impregnated with copper nitrate solution, the solution being added to the carrier in an amount which corresponded to the water absorption of the carrier (incipient wetness method). The impregnated extrudates were dried for 5 hours at 120° C. and then calcined for 2 hours at 520° C. These impregnation and calcination steps were repeated once. The prepared catalyst contained 24.9% by weight of CuO and 75.1% by weight of $SiO_2$, based in each case on the total weight of the catalyst.

Catalyst L $SiO_2$ beads having a diameter of from 3 to 5 mm were impregnated with an ammoniacal copper acetate solution in supernatant solution for 15 minutes. The impregnated beads were then dried for 5 hours at 120° C. and then calcined for 2 hours at 350° C.

These impregnation and calcination steps were repeated once.

The prepared catalyst contained 26.3% by weight of CuO and 73.7% by weight of $SiO_2$, based in each case on the total weight of the catalyst.

Catalyst M

The same carrier as for catalysts G was used for the preparation. Impregnation was carried out by the incipient wetness method, ie. the added amount of the impregnation solution corresponded to the water absorptivity of the carrier. Impregnation was effected several times, as described below.

In the first impregnation step, a solution of calcium nitrate and chromium nitrate was applied, after which drying was carried out for 6 hours at 120° C. and calcination for 2 hours at 700° C.

In the second impregnation step, the copper solution described for catalyst G was used. Thereafter, once again drying was carried out for 6 hours at 120° C. and calcination for 3 hours at 350° C.

The prepared catalyst contained 12.6% by weight of CuO, 5.9% by weight of CaO, 2.7% by weight of $Cr_2O_3$ and 78.8% by weight of $SiO_2$, based in each case on the total weight of the catalyst.

Catalyst N $SiO_2$ extrudates having a diameter of 4 mm were impregnated with a solution of copper nitrate, nickel nitrate and manganese nitrate. The impregnation was carried out by adding the impregnation solution to the carrier in an amount which corresponded to the water absorption of the carrier (incipient wetness method). The extrudates were then dried for 5 hours at 120° C. and then calcined for 2 hours at 520° C.

These impregnation and calcination steps were repeated once.

The prepared catalyst contained 21.3% by weight of NiO, 7.6% by weight of CuO, 2.1% by weight of $Mn_2O_3$ and 69.0% by weight of $SiO_2$, based in each case on the total weight of the catalyst.

Catalyst O $SiO_2$ extrudates having a diameter of 4 mm were impregnated with a solution of copper nitrate, nickel nitrate, manganese nitrate and phosphoric acid. The impregnation was carried out by adding the impregnation solution to the carrier in an amount which corresponded to the water absorption of this material (incipient wetness method). The extrudates were then dried for 5 hours at 120° C. and calcined for 2 hours at 520° C.

These impregnation and calcination steps were repeated once.

The prepared catalyst contained 21.5% by weight of NiO, 7.5% by weight of CuO, 2.0% by weight of $Mn_2O_3$, 1.2% by weight of $H_3PO_4$ and 67.8% by weight of $SiO_2$, based in each case on the total weight of the catalyst.

The mechanical properties were determined as described in Example 1.

EXAMPLE 2.1

Hydrogenation of Hydroxypivalaldehyde (HPA) to Neopentylglycol (NPG)

The starting solution used was aqueous HPA solution having a water content of 24% by weight, based on the total weight of the solution.

The hydrogenation was carried out in a reactor volume of 200 ml with a catalyst volume of 200 ml by the trickle-bed procedure with product recycling (circulation=9.5 l/h). The results are shown in Table II. The catalyst space velocities stated are based on HPA.

TABLE II

| | Catalyst type | Catalyst data | | | | | Hydrogenation conditions | | Hydrogenation result | | | | | |
|---|---|---|---|---|---|---|---|---|---|---|---|---|---|---|
| | | Hardness (N) | Abrasion (%) | CuO (%) | Bulk density (g/l) | Disp. (%) | Space velocity (ml HPA/ ml cat. · h) | T (° C.) | HPA | NPG | i-BuOH | HPN | Conversion | Selectivity |
| F | Precipitate | 70 | 1 | 53.0 | 1125 | 24 | 0.33 | 130 | 0.57 | 88.74 | 1.7 | 4.3 | 99.43 | 89.2 |
| | | | | | | | 0.33 | 140 | 0.51 | 89.14 | 3.4 | 3.1 | 99.49 | 89.6 |
| | | | | | | | 0.4 | 140 | 0.75 | 89.43 | 2.9 | 2.6 | 99.25 | 90.1 |
| G | Cu/$NH_3$ 2 × supernatant | 87 | 2 | 25.6 | 688 | 45 | 0.35 | 130 | 0.89 | 91.5 | 1.15 | 2.35 | 99.11 | 92.3 |
| | | | | | | | 0.45 | 130 | 1.2 | 90.37 | 1.19 | 2.32 | 98.8 | 91.5 |
| H | Cu/$NH_3$ incip. wet. | 24 | n.d. | 23.5 | 625 | 44 | 0.35 | 130 | 0.49 | 89.35 | 0.81 | 3.2 | 99.51 | 89.8 |
| | | | | | | | 0.35 | 140 | 0.42 | 89.3 | 1.41 | 5.7 | 99.58 | 89.7 |
| | | | | | | | 0.44 | 140 | 0.58 | 88.7 | 1.47 | 3.6 | 99.42 | 89.2 |
| I | Cu/$NH_3$ incip. wet | 20.6 | 2 | 24.5 | 740 | 40 | 0.4 | 140 | 0.34 | 89.6 | 1.16 | 3.46 | 99.66 | 89.9 |
| | | | | | | | 0.45 | 150 | 0.21 | 88.75 | 1.7 | 3.47 | 99.79 | 88.9 |
| | | | | | | | 0.55 | 150 | 0.4 | 89 | 1.57 | 3.34 | 99.6 | 89.4 | n.d.: not determined
Disp.: Dispersion
i-BuOH: Isobutanol
HPN: Neopentylglycol hydroxypivalate
Cu/$NH_3$: Ammoniacal copper carbonate solution The hydrogenation of the preferred carbonyl compounds was carried out under the following conditions:

The starting material for the hydrogenation was pumped together with hydrogen, at from 30 to 50 bar, into a heatable tube reactor which was filled with the particular catalyst preparation.

Reactors having a capacity of 75 ml, 200 ml and 1000 ml were used.

The reaction product was let down after the hydrogenation and was collected in a receiver. The analyses were carried out by the gas chromatography method.

The solution to be hydrogenated was pumped linearly over the catalyst bed in the liquid phase or trickle-bed procedure. Alternatively, some of the discharged reaction mixture was pumped back into the reactor before the pressure was let down (circulation procedure).

The space velocities were based on the volumes of the carbonyl compound to be hydrogenated in the solution and of the catalyst bed.

The particular catalyst was either used in the reduced passivated form and fed directly with the hydrogenation solution under hydrogen pressure or employed in its oxidic form and reduced before being metered into the solution to be hydrogenated. The preliminary reduction was carried out using a hydrogen/nitrogen mixture in a ratio of from 1:100 to 1:10 at from 180 to 240° C. for 12 hours.

Compared with comparative catalyst F, the catalyst G prepared by the novel process exhibits both higher dispersion and improved mechanical properties in combination with high conversion and high selectivity. Compared with the catalysts H and I prepared by the incipient wetness method and based on $SiO_2$, the catalyst G prepared on an $SiO_2$ carrier by impregnation in supernatant solution using readily decomposable copper compounds possesses improved mechanical properties, in particular great hardness.

EXAMPLE 2.2

Hydrogenation of an HPA/NPG Mixture to Neopentylglycol (NPG)

Table III shows the results of the hydrogenation of an aqueous solution of equal amounts by weight of HPA and NPG, HPA and NPG together accounting for 76% by weight, based on the total weight of the solution. The reactor volume was 1000 ml and the catalyst volume 700 ml. The reactor was operated by the trickle-bed procedure with product recycling (circulation=10.5 l/h). The catalyst space velocities stated are based on HPA.

Compared with the conventionally prepared catalyst F, the catalyst G prepared by impregnation in supernatant solution using readily decomposable copper compounds exhibits higher dispersion and improved mechanical properties in combination with higher conversion and higher selectivity.

TABLE III

| | Catalyst type | Catalyst data | | | | | Hydrogenation conditions | | Hydrogenation result | | | | | |
|---|---|---|---|---|---|---|---|---|---|---|---|---|---|---|
| | | Hardness (N) | Abrasion (%) | CuO (%) | Bulk density (g/l) | Disp. (%) | Space velocity (ml HPA/ ml cat. · h) | T (° C.) | HPA | NPG | i-BuOH | HPN | Conversion | Selectivity |
| F | Precipitate | 70 | 1 | 53 | 1125 | 24 | 0.25 | 130 | 1.18 | 94.8 | 0.81 | 0.73 | 98.82 | 95.9 |
| | | | | | | | 0.35 | 130 | 1.83 | 93.7 | 0.91 | 0.7 | 98.17 | 95.4 |
| | | | | | | | 0.45 | 130 | 3.8 | 91.5 | 0.93 | 0.87 | 96.2 | 95.1 |
| G | Cu/NH$_3$ 2 × supernatant | 87 | 3 | 35.6 | 688 | 45 | 0.25 | 130 | 0.8 | 95.3 | 0.73 | 0.79 | 99.2 | 96.1 |
| | | | | | | | 0.35 | 130 | 1.15 | 94.9 | 0.68 | 0.93 | 98.85 | 96.0 |
| | | | | | | | 0.45 | 130 | 2.04 | 94.1 | 0.68 | 0.75 | 97.96 | 96.1 |
| J | Cu/NH$_3$ incip. wetness | 70 | 1 | 23.7 | 673 | 31 | 0.25 | 130 | 0.88 | 93.6 | 1.24 | 1.18 | 99.12 | 94.4 |
| | | | | | | | 0.35 | 130 | 2.32 | 92.2 | 1.41 | 1 | 97.68 | 94.4 |
| K | Cu(NO$_3$)$_2$ 2 × supernatant | 41 | 1 | 24.9 | 609 | 5 | 0.25 | 130 | 6.68 | 87.7 | 0.8 | 1.22 | 93.32 | 94.4 |
| L | Cu/(OAc)$_2$ 2 × supernatant | 40 | 4.5 | 26.3 | 638 | 8 | 0.25 | 130 | 1.47 | 93.6 | 0.79 | 0.95 | 98.53 | 95.0 |
| | | | | | | | 0.35 | 130 | 4.43 | 90.7 | 0.7 | 1.07 | 95.57 | 94.9 |
| | | | | | | | 0.45 | 130 | 7.5 | 87.3 | 0.74 | 1.24 | 82.5 | 94.4 | i-BuOH: Isobutanol
HPN: Neopentylglycol hydroxypivalate
Cu/NH$_3$: Ammoniacal copper carbonate solution When the catalysts G and L impregnated in supernatant solution are compared, the catalyst G impregnated with ammoniacal copper carbonate solution has substantial advantages over the catalyst L impregnated with ammoniacal copper acetate solution, both with regard to the dispersion achieved and the resulting mechanical stability and with regard to the conversion and the selectivity at high space velocities.

EXAMPLE 2.3

Hydrogenation of Isobutanal (i-BA) and n-butanal (n-BA) to Isobutanol (i-Bol) and n-butanol (n-Bol)

A mixture of 12.5% by volume of isobutanal and 87.5% by volume of n-butanal was hydrogenated. 20 ppm of KOH were added to the starting mixture. The reaction was carried out in a volume of 75 ml by the liquid phase procedure with linear passage under 50 bar hydrogen pressure. The results are shown in Table IV.

Only catalysts based on SiO$_2$ were compared. The yield is substantially improved at higher space velocities in the case of the catalysts impregnated in supernatant solution using thermally readily decomposable copper compounds.

The catalyst G' shown in Table IV is the catalyst G in reduced/passivated form.

TABLE IV

| Conditions: | | | | | | | | | |
|---|---|---|---|---|---|---|---|---|---|
| Temp.: | | | GC analysis (GC % by area) | | | | | | |
| (° C.) | Cat. | SV: | i-BA | n-BA | i-Bol | n-Bol | Others | Yield | |
| (Starting mixture) | | | 12.40 | 87.10 | — | 0.47 | — | — | |
| 150 | M | 0.33 | 0.22 | 1.27 | 11.40 | 86.60 | 0.51 | 98.00 | |
| 150 | N | 0.33 | 0.00 | 0.00 | 13.09 | 85.84 | 1.07 | 98.93 | |
| 140 | | 0.42 | 0.29 | 1.51 | 12.70 | 82.40 | 3.10 | 95.10 | |
| 150 | | 0.33 | 0.00 | 0.00 | 11.70 | 87.40 | 0.90 | 99.10 | |
| 150 | G | 0.42 | 0.00 | 0.00 | 13.30 | 86.40 | 0.30 | 99.70 | |
| 150 | | 0.50 | 0.00 | 0.00 | 11.50 | 88.10 | 0.40 | 99.60 | |

TABLE IV-continued

| Conditions: | | | | | | | | |
|---|---|---|---|---|---|---|---|---|
| Temp.: | | | GC analysis (GC % by area) | | | | | |
| (° C.) | Cat. | SV: | i-BA | n-BA | i-Bol | n-Bol | Others | Yield |
| 150 | | 0.33 | 0.00 | 0.00 | 12.16 | 87.45 | 0.39 | 99.61 |
| 140 | G' | 0.42 | 0.00 | 0.23 | 12.03 | 87.56 | 0.18 | 99.59 |
| 150 | | 0.50 | 0.00 | 0.19 | 13.00 | 86.53 | 0.28 | 99.53 |

SV: Space velocity (ml of starting material/ml of catalyst · h)

EXAMPLE 2.4

Hydrogenation of 2-hydroxymethyl-2-methylbutanal to 2-methyl-2-ethyl-1,3-propanediol (MEPD)

2-Hydroxymethyl-2-methylbutanal in a solution containing 35% by weight of water and 22% by weight of methanol, based on the total weight of the solution, was hydrogenated in a reactor volume of 75 ml by the trickle-bed procedure with product recycling (circulation=1.2 l/h). A hydrogen pressure of 30 bar prevailed and 55 ml of catalyst were used. The results are shown in Table V.

TABLE V

| | Hydrogenation conditions | | Hydrogenation results | |
|---|---|---|---|---|
| Catalyst type | Space velocity (ml of starting material/ml of cat. · h) | T (° C.) | Conversion (%) | Selectivity (%) |
| G | 0.2 | 130 | 100 | 96 |

EXAMPLE 2.5

Hydrogenation of (8,9),(3,4)-diformyl[5.2.1.0$^{2,6}$] tricyclodecane (TCD-dialdehyde) to (8,9),(3,4)-bis (hydroxymethyl)[5.2.1.0$^{2,6}$]tricyclodecane (TCD-diol)

A solution of 50% by weight of TCD-dialdehyde in tetrahydrofuran was hydrogenated in a reactor volume of 75 ml with linear passage by the liquid phase procedure to give TCD-diol. The stated percentages by weight are based on the total weight of the solution. The results are shown in Table VI.

TABLE VI

| | Hydrogenation conditions | | |
|---|---|---|---|
| Catalyst type | Space velocity (ml of starting material/ml of cat. · h) | T (° C.) | Conversion (%) | Selectivity (%) |
| G | 0.17 | 140 | 100 | 99 |
| | 0.29 | 140 | 99 | 90 |

EXAMPLE 2.7

Hydrogenation of 1-formyl-1-hydroxymethylcyclopentane to 1,1-bis(hydroxymethyl)cyclopentane A solution of 1-formyl-1-hydroxymethylcyclopentane containing 27% by weight of water and 30% by weight of methanol, based on the total weight of the solution, was hydrogenated in a reactor volume of 75 ml with linear passage via the liquid phase procedure. A hydrogen pressure of 50 bar prevailed and 55 ml of catalyst were used. The results are shown in Table VII.

TABLE VII

| | Hydrogenation conditions | | | |
|---|---|---|---|---|
| | Space velocity | | Hydrogenation results | |
| Catalyst type | (ml of starting material/ml of cat. · h) | T (° C.) | Conversion (%) | Selectivity (%) |
| G | 0.3 | 110 | 63 | 89 |
| | 0.3 | 140 | 93.3 | 82 |
| | 0.3 | 145 | 93.3 | 89 |
| | 0.22 | 145 | 99.3 | 91 |

EXAMPLE 2.8

Hydrogenation of 2-ethylhexanal to 2-ethylhexanol

2-Ethylhexanal was hydrogenated in a reactor volume of 75 ml with linear passage by the liquid phase procedure. The hydrogen pressure was 50 bar. The 2-ethylhexanal to be hydrogenated contained from about 3 to 4 ppm of NaOH.

The catalysts G and O were used in the reduced passivated form. Catalyst G' was a catalyst which was used in oxidic form and reduced beforehand in the reactor and which otherwise corresponded to catalyst G. The results are shown in Table VIII.

Here too, it is clear that the catalysts G and G' impregnated in supernatant solution have high conversion and high selectivity in combination with a high space velocity.

TABLE VIII

| | | | GC analysis (GC % by area) | | | | | |
|---|---|---|---|---|---|---|---|---|
| Temp.: (° C.) | Cat. | SV: | Others | enal | anal | anol | Conversion | Selectivity |
| 150 | G | 0.20 | 3.45 | 1.37 | 0.88 | 94.30 | 98.63 | 95.61 |
| 150 | | 0.25 | 3.35 | 3.80 | 1.55 | 41.30 | 96.20 | 94.91 |

TABLE VIII-continued

| | | | GC analysis (GC % by area) | | | | | |
|---|---|---|---|---|---|---|---|---|
| Temp.: (° C.) | Cat. | SV: | Others | enal | anal | anol | Conversion | Selectivity |
| 160 | | 0.25 | 3.85 | 1.49 | 0.76 | 93.90 | 98.51 | 95.32 |
| 160 | | 0.20 | 4.21 | 1.07 | 0.72 | 94.00 | 98.93 | 95.02 |
| 150 | G' | 0.25 | 3.25 | 0.60 | 0.00 | 96.15 | 99.40 | 96.73 |
| 150 | | 0.35 | 2.75 | 0.83 | 0.19 | 96.23 | 99.17 | 97.04 |
| 150 | | 0.50 | 2.82 | 0.85 | 0.63 | 95.70 | 99.15 | 96.52 |
| 150 | O | 0.20 | 3.15 | 0.26 | 4.66 | 91.93 | 99.74 | 92.17 |
| 160 | | 0.20 | 4.58 | 0.05 | 0.70 | 94.67 | 99.95 | 94.72 |
| 160 | | 0.25 | 3.80 | 0.30 | 4.10 | 91.80 | 99.70 | 92.08 | enal: 2-Ethylhex-2-en-1-al
anal: 2-Ethylhexanal
anol: 2-Ethylhexanol

EXAMPLE 2.9

Hydrogenation of Methyl Ethyl Ketone (MEK) to Secondary Butanol

Methyl ethyl ketone was hydrogenated in a reactor having a volume of 75 ml by the trickle-bed circulation procedure to give secondary butanol. The hydrogen pressure was 40 bar. 55 ml of catalyst were used. The results are shown in Table IX.

Table IX

| | Hydrogenation conditions | | | |
|---|---|---|---|---|
| | Space velocity | | Hydrogenation results | |
| Catalyst type | (ml of starting material/ml of cat. · h) | T (° C.) | Conversion (%) | Selectivity (%) |
| G | 0.15 | 130 | 99.5 | 99.4 |
| | 0.25 | 130 | 97.87 | 99.5 |
| | 0.35 | 130 | 96.23 | 98.3 |
| | 0.45 | 130 | 96.75 | 98.5 |

We claim:

1. A process for the preparation of a catalyst, wherein copper is applied on a prefabricated $SiO_2$-containing carrier in the presence or absence of one or more of the elements magnesium, barium, zinc or chromium, wherein the catalyst contains from 5 to 50% by weight copper, calculated as CuO, and from 50 to 95% by weight silicone, calculated as $SiO_2$, based in each case on the total weight of the calcined catalyst, by impregnation of a porous silica carrier with a supernatant aqueous solution of a thermally readily decomposable copper compound and by subsequent drying and calcination, the calcination being carried out at from 200 to 400° C.

2. A process as claimed in claim 1, wherein the sum of the catalyst components copper and silicone, and, if present, magnesium, barium, zinc and chromium is 100% by weight.

3. A process as claimed in claim 1, wherein the catalyst contains from 5 to 30% by weight copper, calculated as CuO.

4. A process as claimed in claim 1, wherein the calcination is carried out at from 250 to 350° C.

5. A process as claimed in claim 1, wherein the catalyst used contains from 5 to 75% by weight, calculated as CuO, of copper and from 95 to 25% by weight, calculated as $SiO_2$, of Si, based in each case on the total weight of the calcined catalyst.

6. A process as claimed in claim 1, wherein the catalyst further comprises one or more of the elements magnesium, barium, zinc or chromium; wherein magnesium is present in an amount of from 0 to 20% by weight, calculated as MgO, barium in an amount of from 0 to 5% by weight, calculated as BaO, zinc in an amount of from 0 to 5% by weight, calculated as ZnO and chromium in an amount of from 0 to 5% by weight, calculated as $Cr_2O_3$, based in each case on the total weight of the calcined catalyst, with the proviso that the sum of the catalyst components copper, silicone and, if present, magnesium, barium, zinc and chromium is 100% by weight.

7. A catalyst, wherein copper is applied on a prefabricated $SiO_2$-containing carrier in the presence or absence of one or more of the elements magnesium, barium, zinc or chromium, wherein the catalyst contains from 5 to 50% by weight copper, calculated as CuO, and from 50 to 95% by weight silicone, calculated as $SiO_2$, based in each case on the total weight of the calcined catalyst, by impregnation of a porous silica carrier with a supernatant aqueous solution of a thermally readily decomposable copper compound and by subsequent drying and calcination, the calcination being carried out at from 200 to 400° C.

8. A catalyst as claimed in claim 7, wherein the catalyst contains 5 to 30% by weight copper, calculated as CuO.

9. A catalyst as claimed in claim 7, wherein the calcination is carried out at from 250 to 350° C.

10. A process for the preparation of an alcohol by catalytic hydrogenation of the corresponding carbonyl compound by elevated temperature and elevated pressure with a catalyst, wherein copper is applied on a prefabricated $SiO_2$-containing carrier in the presence or absence of one or more of the elements magnesium, barium, zinc or chromium, wherein the catalyst contains from 5 to 50% by weight copper, calculated as CuO, and from 50 to 95% by weight silicone, calculated as $SiO_2$, based in each case on the total weight on the calcined catalyst, by impregnation of a porous silica carrier with a supernatant aqueous solution of a thermally readily decomposable copper compound and by subsequent drying and calcination, the calcination being carried out at from 200 to 400° C.

11. A process as claimed in claim 10, wherein the catalyst contains from 5 to 30% by weight copper, calculated as CuO.

12. A process as claimed in claim 10, wherein the calcination being carried out at from 250 to 350° C.

13. A process as claimed in claim 10, wherein the carbonyl compounds are hydrogenated by a pressure from 1 to 150, in a liquid phase.

14. A process as claimed in claim 10, wherein a pH of from 4 to 13 is maintained during hydrogenation.

15. A process as claimed in claim 10, wherein a $C_2-C_{20}$-hydroxy carbonyl compound is used as the carbonyl compound and is converted to the corresponding diol.

16. A process as claimed in claim 10, wherein the carbonyl compounds are hydrogenated at a temperature from 60 to 200° C.

17. A process as claimed in claim 10, wherein a hydroxypropionaldehyde of the formula I

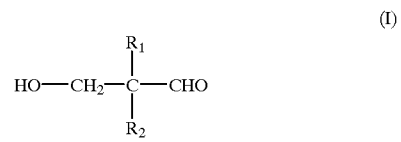

is used as the carbonyl compound and is converted in a 1,3-propanediol of the formula II

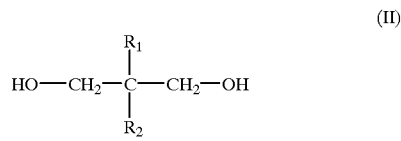

where $R^1$ and $R^2$ are identical on different and are each hydrogen, $C_1-C_{24}$-alkyl or $C_6-C_{20}$-aryl or $C_7-C_{12}$-aralkyl or the two radicals $R^1$ and $R^2$, together with the neighboring carbon atoms, form a 5-membered to 10-membered alicyclic ring.

18. A process as claimed in claim 10, wherein the following are carried out in succession:

Isobutyraldehyde and formaldehyde are reacted in an aqueous medium in the presence of a trialkylamine, the unconverted isobutyraldehyde is separated off from the aqueous solution, preferably by distillation, aqueous reaction solution, which contains hydroxypivalaldehyde, trialkylamine and other impurities and byproducts is hydrogenated with hydrogen in the presence of a copper catalyst and neopentylglycol is recovered from the resulting aqueous phase, prefereably by distillation.

19. A process as claimed in claim 10, wherein a straight-chain or branched aliphatic aldehyde or ketone of 1 to 24 carbon atoms of an $C_3-C_{12}$-ketone is used as the carbonyl compound and is converted into the corresponding alcohol.

20. A process as claimed in claim 10, wherein a straight-chain or branched aliphatic $C_3-C_{12}$-α,β-unsaturated carbonyl compound is used as the carbonyl compound and is converted into the corresponding saturated alcohol.

* * * * *